United States Patent [19]

Eizenhoefer et al.

[11] Patent Number: 5,119,801
[45] Date of Patent: Jun. 9, 1992

[54] PIEZOELECTRIC SHOCK WAVE GENERATOR

[75] Inventors: Harald Eizenhoefer, Johannesberg; Ernst Marlinghaus, Germering, both of Fed. Rep. of Germany

[73] Assignee: Dornier Medizintechnik GmbH, Munich, Fed. Rep. of Germany

[21] Appl. No.: 779,113

[22] Filed: Oct. 15, 1991

Related U.S. Application Data

[63] Continuation-in-part of Ser. No. 307,677, Feb. 2, 1989, abandoned.

[30] Foreign Application Priority Data

Feb. 4, 1988 [DE] Fed. Rep. of Germany ....... 3803275

[51] Int. Cl.⁵ .............................................. A61B 17/22
[52] U.S. Cl. ............................ 128/24 EL; 128/662.03
[58] Field of Search ........ 128/24 AA, 24 EL, 662.03, 128/660.01; 310/335, 337, 311, 313 A

[56] References Cited

U.S. PATENT DOCUMENTS

| | | | |
|---|---|---|---|
| 4,208,602 | 6/1980 | Stoller | 310/335 |
| 4,433,396 | 2/1984 | Johnson et al. | 310/335 |
| 4,462,092 | 7/1984 | Kawabuchi et al. | 128/660.01 |
| 4,686,408 | 8/1987 | Ishiyama | 310/334 |
| 4,783,888 | 11/1988 | Fujii et al. | 310/334 X |
| 5,050,588 | 9/1991 | Grey et al. | 128/24 EL |

FOREIGN PATENT DOCUMENTS 3425992  1/1986  Fed. Rep. of Germany ... 128/24 EL
2140693 12/1984  United Kingdom ........... 128/24 EL Primary Examiner—Lee S. Cohen
Assistant Examiner—Krista M. Pfaffle
Attorney, Agent, or Firm—R. H. Siegemund

[57] ABSTRACT

A piezoelectric shock wave generator for use in medical equipment includes a plurality of piezoelectric elements being electrically interconnected to operate in parallel and mounted on a common carrier of curved configuration; a coupler medium couples shock waves as generated by these piezoelectric generators into the body of a living being, the improvement includes electrical insulation between the piezoelements being in fluid, i.e. liquid or gaseous state, in that each piezoelectric element is surrounded by the fluid in any direction towards any other piezoelectric element; the front ends of the piezoelectric elements may be physically separated, so that the coupler fluid and the isolating fluid are the same, and having a common flow space; alternatively, a membrane in front of all said piezoelectric elements provides electrical interconnection between them and physically separates the isolating fluid from the coupler liquid.

7 Claims, 1 Drawing Sheet

PIEZOELECTRIC SHOCK WAVE GENERATOR

This is a continuation-in-part of co-pending application Ser. No. 307,677 filed on Feb. 2, 1989 now abandoned.

BACKGROUND OF THE INVENTION

The present invention relates to piezoelectric generation of shock waves particularly for medical purposes, under inclusion of a plurality of piezoelectric elements on a carrier, and under appropriate coupling of an energy source to the elements on one hand and isolation of the elements from each other on the other hand.

German Patent 34 25 992 describes a piezoelectric transducers for the destruction of concrements in the body of a living being under inclusion of a spherical calotte having on its convex front arranged piezoelectric element and being characterized by the fact that the wave impedances of the calotte material as well as of the ceramic material do not significantly deviate from each other, and the rear surface is geometrically configured and/or coated so that reflected sound waves will not be focused. As per the last sentence in that patent, the piezoelectric elements are isolated from each other by casting them in an electrically insulating material.

DESCRIPTION OF THE INVENTION

It is an object of the present invention to provide a new and improved device of the type that are known and to improve particularly on construction as per the above identified patent bearing in mind that the main problem is to generate as strong shock waves as possible.

In accordance with the preferred embodiment of the present invention it is suggested to provide structure such that the insulation and isolation electrically as well as from the point of view of agitation of the piezoelectric elements from each other is provided through a fluid, i.e. a gas or liquid having an insulation strength that is better than the insulation strength of air, that is a breakthrough strength higher than about 5 kilovolts per millimeter. The piezoelectric elements are mounted on a concavely shaped carrier such that flow space between them remains. One will use preferably a metal membrane on the front (inwardly pointing) ends of the piezoelectric elements, being as far as impedance is concerned matched to these elements and providing physical separation between the isolating fluid and any coupler liquid on the inside of the spherically shaped space of the membrane. This liquid couples the transducers to the body of the patient; and the membrane separates the coupler liquid from the insulating fluid. If the membrane is not provided for, then the two fluids have to be the same; they share a common flow space.

It was found that the fluid insulation provides in fact a drastic increase in the strength against voltage breakthrough of the device. One can use as far as applicant ascertains any known liquidous or gaseous insulating materials. It is believed that the fluid state is the controlling aspect whereby specifically the direct abutment of the fluid against the piezoelectric elements is the primary agent which, in accordance with the invention, reliably prevents the formation of any kind of air gap between insulation and piezoelectric transducer. Such a gap could result in the formation of electric leakage currents. Avoidance of that air gap between solid material of the piezoelectric device on one hand and any kind of solid insulation is believed to be the primary agent of effectiveness of invention. Preferred insulation fluid is provided by fluorocarbonates, oil or gaseous material such as sulphurhexafluoride or fluorocarbon.

As stated, in principle the inventive shock wave source may be provided with or without a membrane on the front side of the piezo elements facing the concavity. If the membrane is used it should be made of metal that is in contact with the front side (electrodes) of all the piezo elements. As stated, the membrane must be made of a material having a suitable acoustic impedance, and which for a particular thickness fulfills the function and requirement of impedance matching between piezoceramic on one hand, and the coupler fluid such as water or a gel on the inside of the calotte shaped configuration, on the other hand. A very suitable material is, e.g. Mg Mn2 with a number 3.5200 in accordance with DIN 1729. This material of the membrane must be dimensioned to fulfill the requirement $Z=[Z_1.Z_3]^{0.5}$ whereby Z is the effective acoustic impedance, $Z_1$ is the acoustic impedance of the piezoelements, and $Z_3$ is the acoustic impedance of the coupling medium. The desired and preferred membrane thickness is to be lambda/4 wherein lambda is the wavelength of the preferred spectral component of the acoustic pulse that is produced by the piezoelectric elements.

Conceivably, an adaptor or impedance matching body of generally small dimensions may be provided in front of each individual piezoelement. The electrical connection between the piezoelement and the membrane if present and between the elements themselves as well as the rear contact making obtains through a conductive coating on the carrier as a backing the connection may be made through soldering, bonding with an electrically conductive adhesive, ultrasonic welding but even simple force and press working may be sufficient. In the case of soldering or ultrasonic welding it is, of course, necessary to make sure that the welding temperature remains well below the Curie temperature. Contact making on one side or the other, if a membrane and/or a coating is not provided for, may obtain through wire loops, mesh layers or the like made of electrically conductive wires, filaments or the like. In one preferred form the coupled medium isolation is the same in which case the separating membrane is no longer necessary. It was found that this way of operating increases the power output further.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates an outer concavely shaped carrier T which may be spherical calotte for purposes of focusing shock waves in the geometric center of that carrier T. On the inside the surfaces T2 are mounted individual piezoelectric elements P, in a regular pattern, but it is essential that they are spaced apart to leave chamber and flow space around each and all of these piezoelectric elements. The distance between them is relatively small. By way of example, the distance is roughly equivalent to the width of the elements themselves or even smaller. That flow space between the piezoelectric element P is filled with insulating liquid I. That insulating liquid has a breakthrough strength better than air and prevents voltage breakthough along any of the piezoelectric elements P. The breakthrough voltage must be higher than about 5 kilovolts per millimeter.

Figure 1:
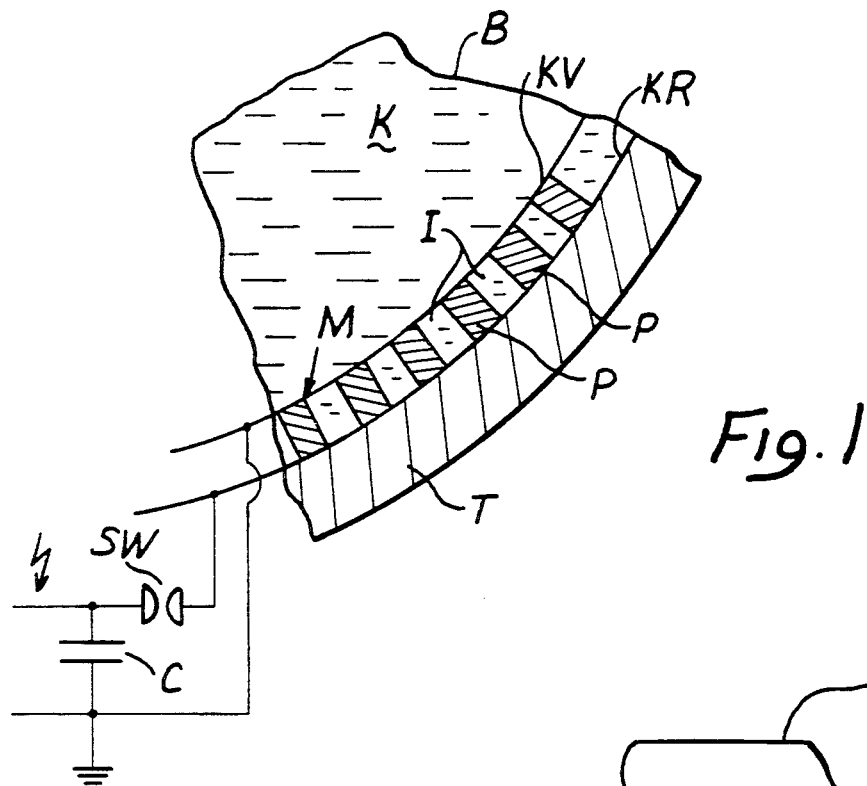
FIG. 1 and FIG. 2-3 are cross-sections through differently constructed preferred embodiments of the present invention showing in each instance just a certain portion of the overall device.

The inside surface T2 as mentioned is covered with a coating or layer KR being electrically conductive and providing a particular voltage potential to each and all of the elements P. The front of each individual element P is provided with a metal layer KV which, in turn, and in each instance is in direct electrical contact with a spherically shaped membrane M. KV, however, may not necessarily be a separate element but just the front electrode of each piezoelectric element and, in this case, these electrodes are directly in contact making engagement with the membrane M. The membrane M is made of a metal, preferred a material that was mentioned in the introduction. The coating KR is just a good electrical conductor and any specific acoustic properties are not necessary.

Reference character K refers to a coupler medium (water or a gel) which is, for example, confined by a cushion cover B made of a flexible material. The entire device will be placed against the body of a human being and under such conditions that the center of the curvatures of the concentric arrangement of piezoelectric elements, carrier, and membrane locates in a concrement to be comminuted. Basically of course the task exists to couple acoustically the piezoelectric elements P to that concrement in an efficient manner as possible. There should be very low losses as far as the shock wave production and transmission of ultrasonic energy is concerned.

The circuit now is completed in such a manner that as stated membrane M is connected to ground. A capacitor C is provided such that its non-grounded side, through a switch SW, causes an arc to discharge and apply a high voltage pulse to the layer KR. This brief pulse causes all of the piezoelectric elements P in parallel to be contracted shortly (or expanded), depending on the particular configuration of these elements and that contraction or expansion is transmitted as a common motion upon the membrane M resulting in a shock wave having a spherical wavefront and converging to the center of the spheres. The shock wave when focused in a concrement such as a kidney stone or a gall stone must be sufficiently strong at that point o convergence, so that its energy suffices to comminute the concrement.

In accordance with the invention the insulating I is a liquid or gas which in effect is confined between the membrane M on one hand and the carrier T on the other hand. The liquid provides insulation of the elements P from each other in a gapfree fashion.

Figure 2:
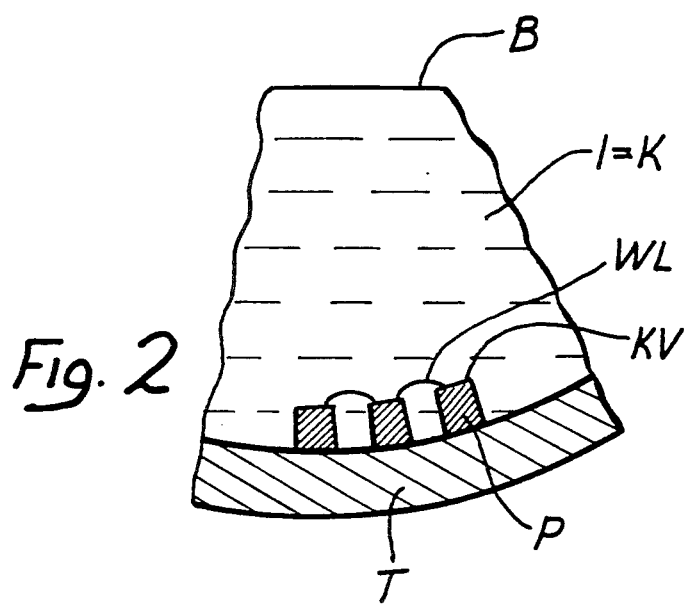

FIG. 2 illustrates the combining of the coupler function of liquid K and the isolating function of the liquid I. This is symbolically represented in the drawing through the equation $I=K$. There is no membrane M, and the front ends of the piezoelectric elements P are not interconnected in a confining fashion but there is, of course, a connection provided between the contact layers KV (or electrodes) in front of each of the elements P which wire loops WL provide for electrical connection, ultimately to the electric circuit that stimulates the device in a manner shown in FIG. 1.

It is, of course, necessary in the case of FIG. 2, to consider that the liquid must have an acoustic coupler function and not just the insulating function as was mentioned which puts certain constraints on that liquid. It was found that silicon oil or mineral oils are well suited to provide both the acoustic coupling function and the electric isolating function. While this may be regarded to some extent as a compromise it is found that the configuration is such that the avoidance of the membrane has a beneficial effect as far as the power output of the device as concerned.

Figure 3:
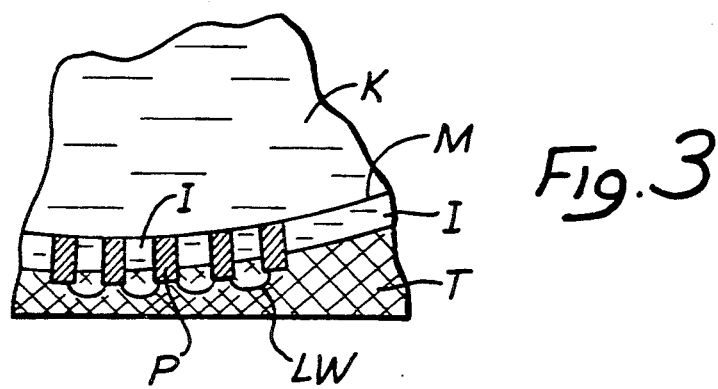

FIG. 3 illustrates a further modification. While the carrier E in FIG. 2 is the same as in FIG. 1, the carrier T' in FIG. 3 is different in that it is a casting material into which the rear ends of the piezoelectric elements P are stuck; they are, of course, electrically interconnected separately through loops LW, because in this case the carrier T' is not an electrical conductor which it never has to be but it also does not provide any kind of layer equivalent to KV in FIG. 1. The front of the piezoelectric elements can be configured as shown in FIG. 2 but in this case a membrane M is shown similar to the configuration of FIG. 1. The membrane is of course separate from the isolating liquid or gas I.

The invention is not limited to the embodiments described above but all changes and modifications thereof, not constituting departures from the spirit and scope of the invention, are intended to be included.

We claim:

1. In a piezoelectric shock wave generator for use in medical equipment and including a plurality of piezoelectric elements being electrically interconnected to operate in parallel and mounted on a common carrier, there being a coupler medium for coupling shock waves as generated by these piezoelectric elements into the body of a living being, wherein the improvement comprises an electrical insulation between the piezoelectric elements being in a fluid state, in that each of said piezoelectric elements is surrounded by the fluid insulation, and in any direction towards any other of the piezoelectric elements, said insulation having a breakthrough strength in excess of about 5 KV/mm, being larger than the breakthrough strength of air.

2. Generator as in claim 1 wherein front ends of the piezoelectric elements are physically separated, said coupler medium and said insulation fluid being the same and having a common flow space.

3. Generator as in claim 1 there being a membrane in front of all said piezoelectric elements providing electrical interconnection between them and physically separating said insulation fluid from said coupler medium.

4. Generator as in claim 2 further comprising individual impedance matching devices in front of each of said piezoelectric elements.

5. Generator as in claim 1, wherein rear ends of said piezoelectric elements are embedded in said carrier.

6. Generator as in claim 1 further comprising wire loops interconnecting front ends of adjacent piezoelectric elements.

7. In a piezoelectric shock wave generator for use in medical equipment and including a plurality of piezoelectric elements being electrically interconnected to operate in parallel and mounted on a common carrier, there being a coupler liquid for coupling shock waves as generated by these piezoelectric elements into the body of a living being, wherein the improvement comprises an electrical insulation between the piezoelectric elements being a liquid, in that each of said piezoelectric elements is surrounded by the liquid, and in any direction towards any other of the piezoelectric elements, said insulation liquid having a breakthrough strength in excess of about 5 KV/mm which is larger than the breakthrough strength of air.

* * * * *